(12) United States Patent
Tota et al.

(10) Patent No.: US 9,771,401 B2
(45) Date of Patent: Sep. 26, 2017

(54) **GREEN FLUORESCENT PROTEIN (GFP) PEPTIDES FROM *RHACOSTOMA***

(71) Applicants: Michael R. Tota, North Brunswick, NJ (US); William W. Ward, North Brunswick, NJ (US)

(72) Inventors: Michael R. Tota, North Brunswick, NJ (US); William W. Ward, North Brunswick, NJ (US)

( * ) Notice: Subject to any disclaimer, the term of this patent is extended or adjusted under 35 U.S.C. 154(b) by 0 days.

(21) Appl. No.: 14/777,311

(22) PCT Filed: Mar. 17, 2014

(86) PCT No.: PCT/US2014/030345
§ 371 (c)(1),
(2) Date: Sep. 15, 2015

(87) PCT Pub. No.: WO2014/145554
PCT Pub. Date: Sep. 18, 2014

(65) Prior Publication Data
US 2016/0024160 A1    Jan. 28, 2016

Related U.S. Application Data

(60) Provisional application No. 61/799,464, filed on Mar. 15, 2013.

(51) Int. Cl.
*C07K 14/435*     (2006.01)
*G01N 33/58*     (2006.01)

(52) U.S. Cl.
CPC ...... *C07K 14/43595* (2013.01); *G01N 33/582* (2013.01); *C07K 2319/60* (2013.01); *G01N 2333/43595* (2013.01)

(58) Field of Classification Search
None
See application file for complete search history.

(56) References Cited

U.S. PATENT DOCUMENTS

2005/0272111 A1    12/2005    Bryan et al.
2007/0298412 A1    12/2007    Lukyanov et al.

OTHER PUBLICATIONS

International Search Report, in PCT International Application No. PCT/US14/30345, dated Sep. 3, 2014.
Written Opinion of the International Searching Authority, in PCT International Application No. PCT/US14/30345, dated Sep. 3, 2014.
ASP2014 Final Online Program and Abstracts, 37th Meeting of the American Society for Photobiology, San Diego, California, Jun. 2014 [Online], Retrieved from the Internet <URL: http://www.photobiology.org/UserFiles/File/ASP2014%20Final%20Online_Program.pdf>.

*Primary Examiner* — Kagnew H Gebreyesus
(74) *Attorney, Agent, or Firm* — Carter, DeLuca, Farrell & Schmidt, LLP

(57) ABSTRACT

The present technology is directed to the nucleic acid molecule encoding novel fluorescent proteins, in particular, green fluorescent proteins (GFPs), such as those that may be isolated from an organism of genus *Rhacostoma*, as well as compositions comprising the same and methods for analyzing a physiologically active substance in a cell wherein the fluorescent proteins are expressed in the cell.

10 Claims, 13 Drawing Sheets

Figure 1: DNA sequence of fluorescent protein – SEQUENCE 1

>seq1

ATGAGCACTGGAAAGACTGGTAAAATGCTCTTCCAAC

AAGAGATTCCTTTCATCGTGTCATTAGATGGTGAAGTTGAGGGAGAAATATTTGGTGTCA

GAGGGGAAGGATATGGAGATGCTACCATTGGTAAGATAGACATCACCTATCATTGTATCA

CCGGGAAATTGCCAGTACCATGGCCAACTATTTTAACCTCACTGGCCTATGGAGTCACAT

GTTTTGCGAAATATCCCGAAAATGTCAACGATTTCTTTAAAGATTGTATGCCTGAAGGCT

ACGTGCAGGAGAGGACTATCTCGTTTGAAGGTGAAGGCGTCTATAAGACACGAGCAGAAG

TCACTTACGAAAGTGGAACTGTGTACAACAGAGTCCAATTGACTGGCTCTGGCTTCAAGA

GAAATGGGAACATCCTAGCCAAGAAATTGGAATTCAATTTCAATCCAAGTTGCAGTTATG

TTCTTCCAGACGCAGAGAACAATGGAATAAACCTTGTCTTTAAACAGGTGCACAATATCG

TTGGAGGTGATTTCATTATTGGCGAGCACGATCAGCAAACCAGGCCCATTGGCAAGGGTC

CGGACGCCCTCCCGCATTATCACCATATTCAGGTTCAAACAGTCCTCTCAAAAGACCCTG

AGGAACCCAGAGACAATATGAGGATGGTGGAATACATCACTGCCGTTGACTGCGACACTG

CTTATAATAAGGAGGATAA

Figure 2: Protein sequence of fluorescent protein – SEQUENCE 2

>seq2

MSTGKTGKMLFQQEIPFIVSLDGEVEGEIFGVRGEGYGDATIGKIDITYHCITGK

LPVPWPTILTSLAYGVTCFAKYPENVNDFFKDCMPEGYVQERTISFEGEGVYKTRAEVTY

ESGTVYNRVQLTGSGFKRNGNILAKKLEFNFNPSCSYVLPDAENNGINLVFKQVHNIVGG

DFIIGEHDQQTRPIGKGPDALPHYHHIQVQTVLSKDPEEPRDNMRMVEYITAVDCDTAYN

KGG

Figure 9

Figure 12 Sequence 3 DNA sequence for V204Y/M221T mutant

> V204Y M221T

ATGAGCACTGGAAAGACTGGTA

AAATGCTCTTCCAACAAGAGATTCCTTTCATCGTGTCATTAGATGGTGAAGTTGAGGGAG

AAATATTTGGTGTCAGAGGGGAAGGATATGGAGATGCTACCATTGGTAAGATAGACATCA

CCTATCATTGTATCACCGGGAAATTGCCAGTACCATGGCCAACTATTTTAACCTCACTGG

CCTATGGAGTCACATGTTTTGCGAAATATCCCGAAAATGTCAACGATTTCTTTAAAGATT

GTATGCCTGAAGGCTACGTGCAGGAGAGGACTATCTCGTTTGAAGGTGAAGGCGTCTATA

AGACACGAGCAGAAGTCACTTACGAAAGTGGAACTGTGTACAACAGAGTCCAATTGACTG

GCTCTGGCTTCAAGAGAAATGGGAACATCCTAGCCAAGAAATTGGAATTCAATTTCAATC

CAAGTTGCAGTTATGTTCTTCCAGACGCAGAGAACAATGGAATAAACCTTGTCTTTAAAC

AGGTGCACAATATCGTTGGAGGTGATTTCATTATTGGCGAGCACGATCAGCAAACCAGGC

CCATTGGCAAGGGTCCGGACGCCCTCCCGCATTATCACCATATTCAGTATCAAACAGTCC

TCTCAAAAGACCCTGAGGAACCCAGAGACAATATGAGGACGGTGGAATACATCACTGCCG

TTGACTGCGACACTGCTTATAATAAAGGAGGATAA

Figure 13 Sequence 4 Protein sequence for V204Y/M221T mutant

> V204Y M221T

MSTGKTGKMLFQQEIPFIVSLDGEVEGEIFGVRGEGYGDATIGKIDITYRCITGK
LPVPWPTILTSLAYGVTCFAKYPENVNDFFKDCMPEGYVQERTISFEGEGVYKTRAEVTY
ESGTVYNRVQLTGSGFKRNGNILAKKLEFNFNPSCSYVLPDAENNGINLVFKQVHNIVGG
DFIIGEHDQQTRPIGKGPDALPHYHHIQYQTVLSKDPEEPRDNMRTVEYITAVDCDTAYN
KGG

US 9,771,401 B2

GREEN FLUORESCENT PROTEIN (GFP) PEPTIDES FROM *RHACOSTOMA*

CROSS-REFERENCE TO RELATED APPLICATIONS

This application is a national stage of International Application No. PCT/US14/30345, filed Mar. 17, 2014, which claims benefit of U.S. Provisional Application No. 61/799,464, filed Mar. 15, 2013. The entire contents of each and every foregoing application are hereby incorporated herein by reference.

SEQUENCE LISTING

The instant application contains a Sequence Listing which has been submitted electronically in ASCII format and is hereby incorporated by reference in its entirety. Said ASCII copy, created on Jun. 30, 2014, is named 22900011.003_SL.txt and is 23,318 bytes in size.

BACKGROUND

Green-fluorescent proteins (GFPs) have been found to be useful tools for genetically labeling proteins, enzymes, antibodies, cells, tissues, organs, and organisms. In addition, GFP is widely used as a brilliant and sensitive reporter in biochemical assays. GFP's desirability comes from its intrinsic fluorescence and the fact that GFP can be introduced genetically. GFP makes its own intrinsic chromophore (fluorophore) without any required enzymes or cofactors other than molecular oxygen. (Prasher DC, Eckenrode VK, Ward WW, Prendergast FG, Cormier MJ. Primary structure of the *Aequorea victoria* green-fluorescent protein. Gene. 1992 Feb. 15;111(2):229-33; Chalfie M, Tu Y, Euskirchen G, Ward W W, Prasher D C. Green fluorescent protein as a marker for gene expression. Science. 1994 Feb. 11;263 (5148):802-5.)

The known GFPs have mostly originated from members of the phylum Cnidaria (which includes jellyfish, sea pansies, corals, sea pens, and hydroids). As biochemical markers, most of the cloned GFPs have specific niches (Shaner N C, Steinbach P A, Tsien R Y. A guide to choosing fluorescent proteins. Nat Methods. 2005 Dec.;2(12):905-9.). For example, as a group, they span the color range from blue to red in their fluorescence emission properties and they come as monomers, dimers, or tetramers. There are differences in photostability, pH sensitivity, extinction coefficient, and fluorescence quantum yield. Some express better than others in heterologous organisms and some seem ideally suited for certain instrument systems (for example, fluorescence activated cell sorting (FACS), confocal microscopy, argon ion laser excitation, fluorescence resonance energy transfer (FRET), and western blots). The abbreviation GFP is usually used to refer to the proteins isolated from, or cloned from, the jellyfish *Aequorea victoria*, or on occasion to the sea pansy or *Renilla reniformis*.

To fit into a particular niche, physical and spectral properties of a given fluorescent protein (FP) can be altered by mutagenesis (selected reviews: Heim R, Tsien R Y. Engineering green fluorescent protein for improved brightness, longer wavelengths and fluorescence resonance energy transfer. Curr Biol. 1996 Feb. 1;6(2):178-82; Shaner N C, Patterson G H, Davidson M W. Advances in fluorescent protein technology. J Cell Sci. 2007 Dec. 15;120(Pt 24): 4247-60.). But, the degree of alteration possible seems to be related to the starting amino acid structure of the "parent" protein. Sometimes this intrinsic sequence is called the "scaffold." It is proposed herein that GFPs with very different inherent scaffolds could be genetically modified in ways that other GFPs (having different scaffolds) cannot be modified. Random or directed mutagenesis of a truly novel GFP has been developed herein.

SUMMARY OF THE DISCLOSED TECHNOLOGY

In certain embodiments, the present technology is directed to novel fluorescent proteins, for example, green fluorescent proteins (GFPs) such as those that are isolated from *Rhacostoma*, a jellyfish; as well as compounds comprising such fluorescent proteins.

In other embodiments, the present technology is directed to cloning of the novel fluorescent proteins, as well as mutants and methods for preparing and using the same in research, diagnostic and therapeutic applications.

BRIEF DESCRIPTION OF THE DRAWINGS

FIG. 1 shows the DNA sequence of a fluorescent protein developed as described herein, according to certain embodiments, and indicated as SEQ ID NO: 1.

FIG. 2 shows a protein sequence of a fluorescent protein developed as described herein, according to other embodiments. This is SEQ ID NO: 2 and is deduced from SEQ ID NO: 1.

FIG. 9 shows alignment of GFP (*Aequorea victoria* gi|1169893) (SEQ ID NO: 14) with fluorescent proteins, or GFP-like proteins, from *Rhacostoma* (seq 2) (SEQ ID NO:

2), coerulescens (Aequorea coerulescens gi|34421676) (SEQ ID NO: 15), magnificus (Aldersladia magnificus gi|183186849) (SEQ ID NO: 16), macrodactyla (Aequorea macrodactyla gi|18175254) (SEQ ID NO: 17), Obelia (Obelia sp. MH-2011 gi|342221051) (SEQ ID NO: 18), Clytia_gregaria (Clytia gregaria gi|298257355) (SEQ ID NO: 19), and Phialidium (Phialidium sp. SL-2003 gi|40365351) (SEQ ID NO: 20). Introduced gaps are shown by dots. Dark shading shows identity to the consensus sequence, light shading shows similarity to the consensus sequence. Sequences were aligned with ClustalX (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007) Clustal W and Clustal X version 2.0. Bioinformatics, 23:2947-2948).

Figure 10:
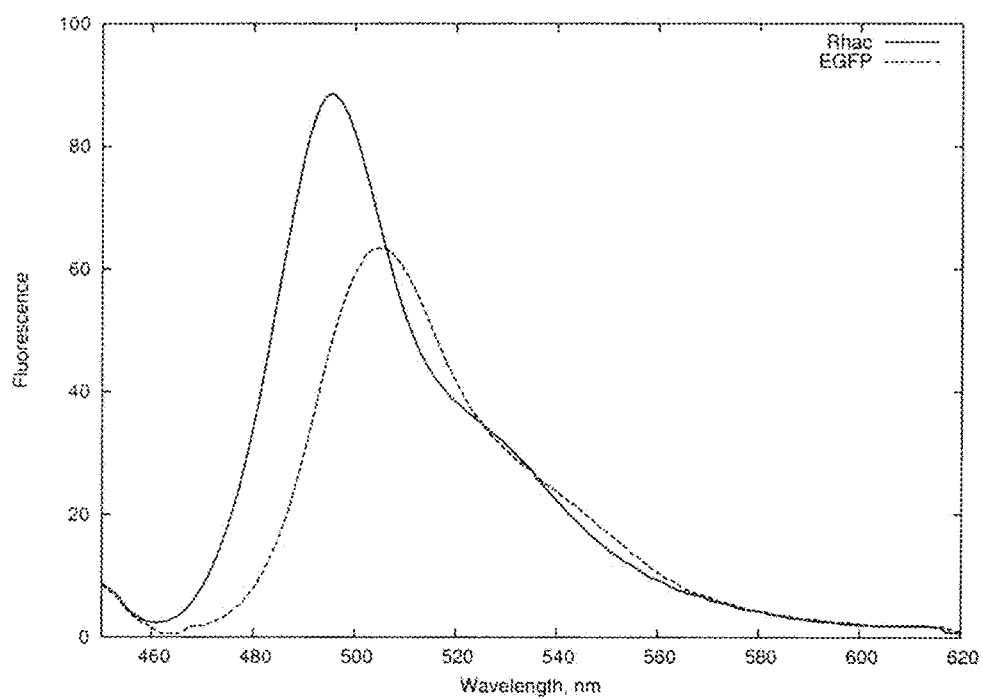

FIG. 10 shows fluorescence emission spectra of the Rhacostoma FP (solid line) and Enhanced Green Fluorescent Protein (EGFP, Heim R, Cubitt A B, Tsien R Y. Improved green fluorescence. Nature. 1995 Feb. 23;373(6516):663-4) (dashed line). Rhacostoma FP and EGFP were diluted in 10 mM Tris pH 8.0 buffer to give an absorbance of 0.046 at 450 nm. A fluorescence emission spectrum was collected using a Gilford Fluoro IV spectrofluorometer with the excitation monochromator set to 450 nm. Fluorescence was recorded in arbitrary units.

Figure 11:
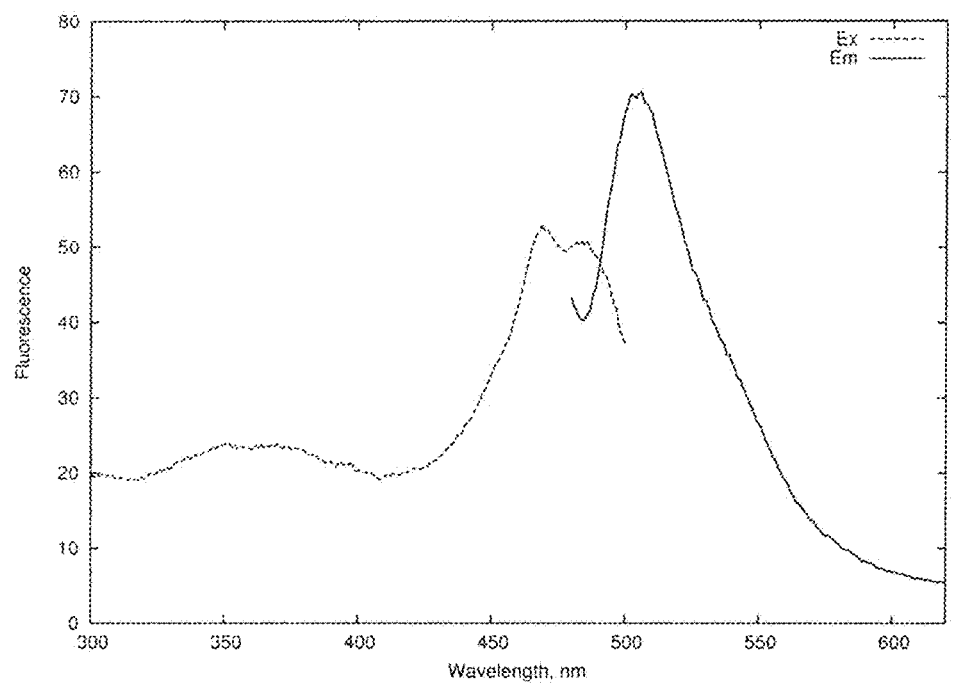

FIG. 11 shows an excitation spectrum (dashed line) and emission spectrum (solid line) of Rhacostoma mutant protein V204Y/M221T. Washed E. coli cells were diluted into 10 mM Tris pH 8.0 buffer to an optical density of 0.1 at 600 nm. The fluorescence spectra were collected with a Gilford Fluoro IV spectrofluorometer with the PMT voltage set to 600. An emission wavelength of 530 nm was used for the excitation spectrum and an excitation of 460 nm was used for the emission spectrum. Escherichia coli cells expressing wild type Rhacostoma FP required 400 volts at the PMT to elicit a similar signal intensity, corresponding to an approximate 20 fold difference in intensity.

FIG. 12 shows the DNA sequence of the V204Y/M221T mutant developed as described herein, according to certain embodiments, and indicated as SEQ ID NO: 3.

FIG. 13 shows the protein sequence of the V204Y/M221T mutant developed as described herein, according to certain embodiments, and indicated as SEQ ID NO: 4.

DETAILED DESCRIPTION

The present technology generally relates to novel fluorescent proteins, such as green fluorescent proteins (GFPs), which have found to be useful markers for gene expression; as well as compounds comprising such green fluorescent proteins and methods of preparing and using the same. In particular, in certain embodiments, the present technology is directed to methods and processes for preparing monomers and dimers of such fluorescent proteins.

Herein, the nucleic acid sequences and the corresponding amino acid sequences of novel fluorescent proteins have been discovered and isolated. The novel fluorescent proteins may be derived from a previously uncharacterized jellyfish of the genus Rhacostoma, including Rhacostoma atlantica. In the GFPs derived in certain embodiments herein, the sequences were identified by PCR using degenerate primers corresponding to conserved amino acid regions of GFPs from other Leptomedusae. In certain embodiments, a resulting amino acid sequence has only a 55% identity with its closest match from a BLAST search. Expression in E. coli confirmed that the nucleic acid sequence encodes for a fluorescent protein.

Figure 9:
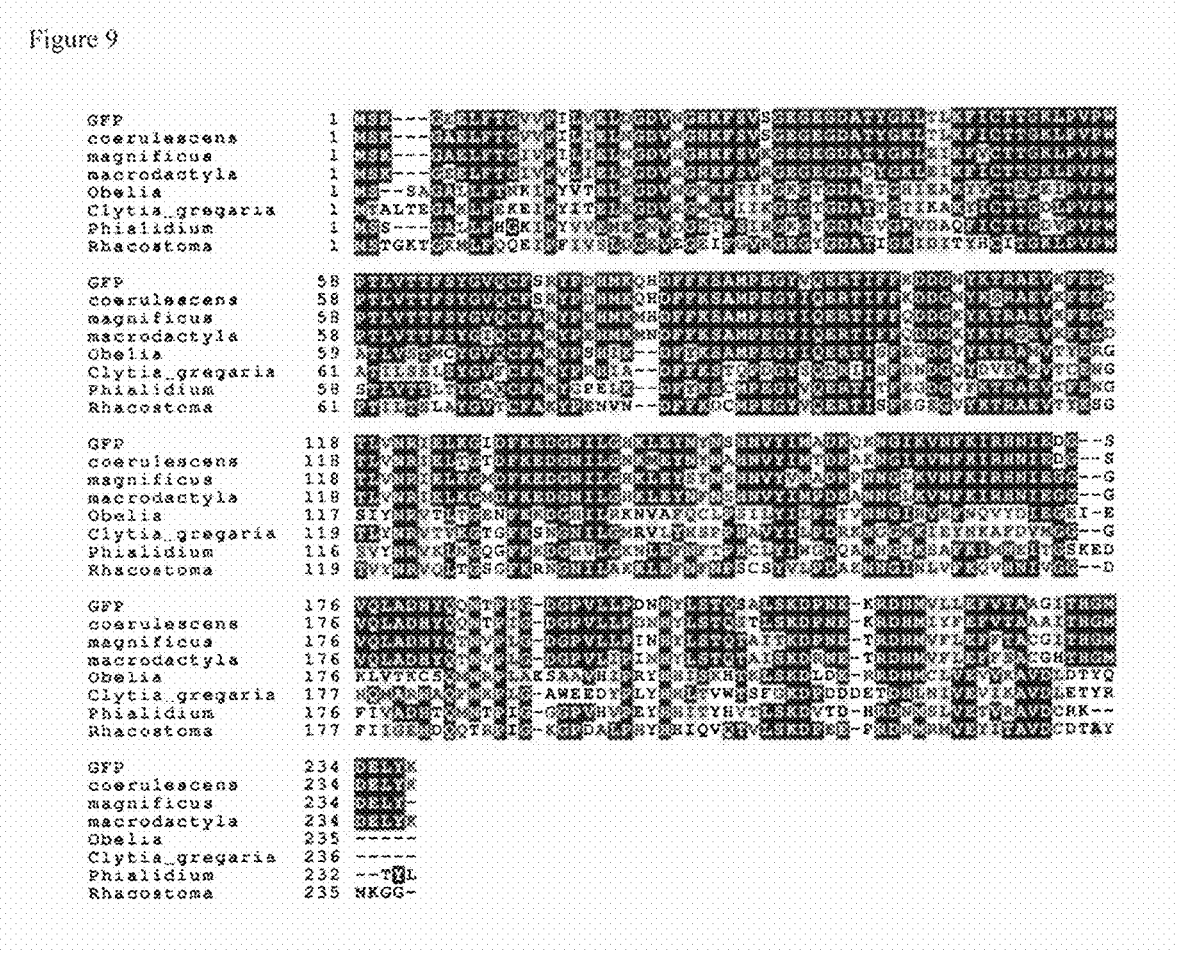

Rhacostoma GFP has an amino acid scaffold that is different from any of its taxonomic relatives. While some GFPs differ from others by as few as 2 amino acids, the GFP in certain embodiments herein differs from its nearest neighbor by more than 100 amino acids (45% dissimilar in amino acid sequence). A sequence comparison is shown in FIG. 9.

In a non-limiting example, a specimen of Rhacostoma atlantica was collected off the coast of New Jersey. Total RNA was isolated with a MasterPure Complete DNA and RNA Purification Kit (Epicentre) and a cDNA library was synthesized and amplified with a SMARTer PCR cDNA synthesis kit (Clonetech). Degenerate PCR primers were designed based on conserved amino acid regions of GFPs from other Leptomedusae. PCR was performed on the cDNA library with the degenerate primers and a PCR primer incorporating a poly T sequence to prime on the 3' end of the cDNA molecule. PCR products were ligated into a pGEM vector and transformed into E. coli. Plasmids were prepared from the E. coli, sequenced, and examined for GFP like sequences. The resulting 3' fragment of the DNA corresponding to the novel fluorescent protein was then used to design a set of reverse primers. In order to provide an additional 5' template, the cDNA library was ligated into a pGEM vector. PCR was performed on the ligation mixture using a primer from the 3' end of the DNA corresponding to the novel fluorescent protein and a primer corresponding to vector sequence at the 5' end of the incorporation site. The resulting 5' fragment of the DNA corresponding to the novel fluorescent protein was then used to generate a new set of forward primers. The full length sequence was obtained by PCR on the original cDNA library using a set of primers from the DNA corresponding to the novel fluorescent protein obtained above. The PCR product was cloned into a pGEM vector and sequenced.

BLAST searches were performed with BLASTP (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.) Sequence comparisons were performed with ClustalX (Larkin, M. A., Blackshields, G, Brown, N. P., Chenna, R., McGettigan, P. A., McWilliam, H., Valentin, F., Wallace, I.M., Wilm, A., Lopez, R., Thompson, J. D., Gibson, T. J., Higgins, D. G. (2007) Clustal W and Clustal X version 2.0. Bioinformatics, 23:2947-2948.)

For protein expression, the cDNA was subcloned into a pBAD vector between the Nde I and Kpn I sites. The resulting vector was used to transform E. coli DH10B cells which were then selected on plates with carbenicillin and L-arabinose. A fluorescent colony was selected and grown overnight at 37C in LB media with carbenicillin. The overnight culture was diluted 24-fold into fresh LB media with carbenicillin and allowed to grow for 3 hours at 37 degrees C. The culture was then induced with the addition of 0.1% L-arabinose and allowed to grow for 22 hours at room temperature.

Figure 3:
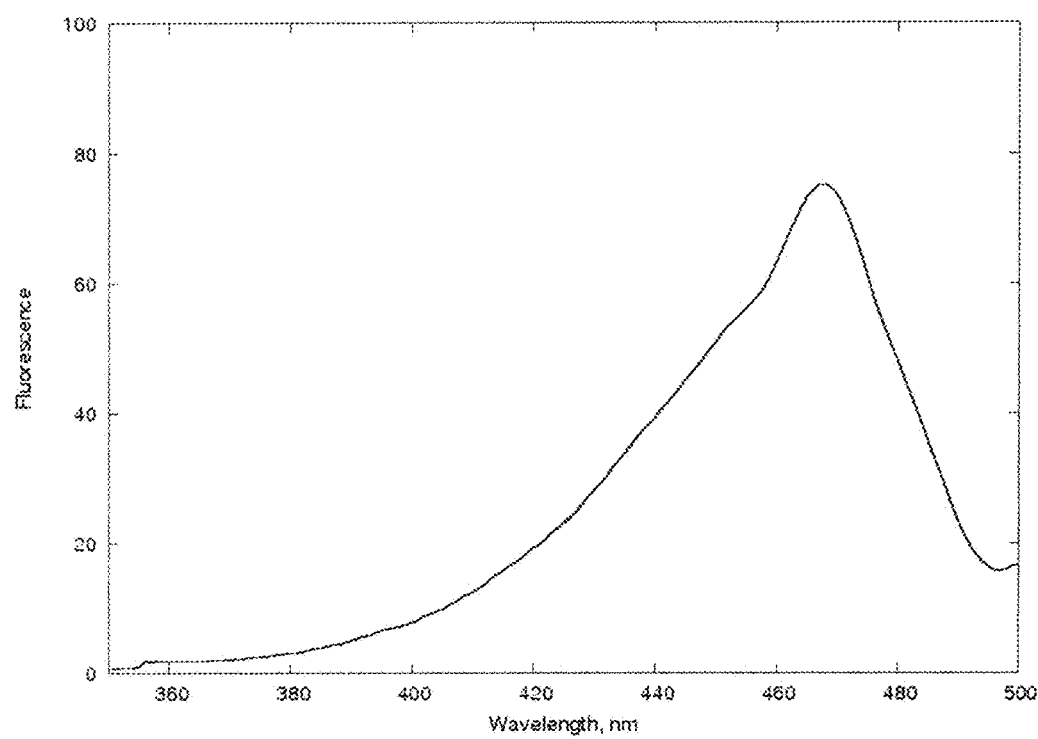
FIG. 3 shows an excitation spectrum of a fluorescent protein of SEQ ID NO: 2. Extract from *E. coli* expressing *Rhacostoma* GFP was diluted in 10 mM Tris pH 8.0 buffer to give an absorbance of 0.05 at 466 nm. A fluorescence excitation spectrum was collected using a Gilford Fluoro IV spectrofluorometer. The emission monochromator was set to 505 nm. Fluorescence was recorded in arbitrary units.
Figure 4:
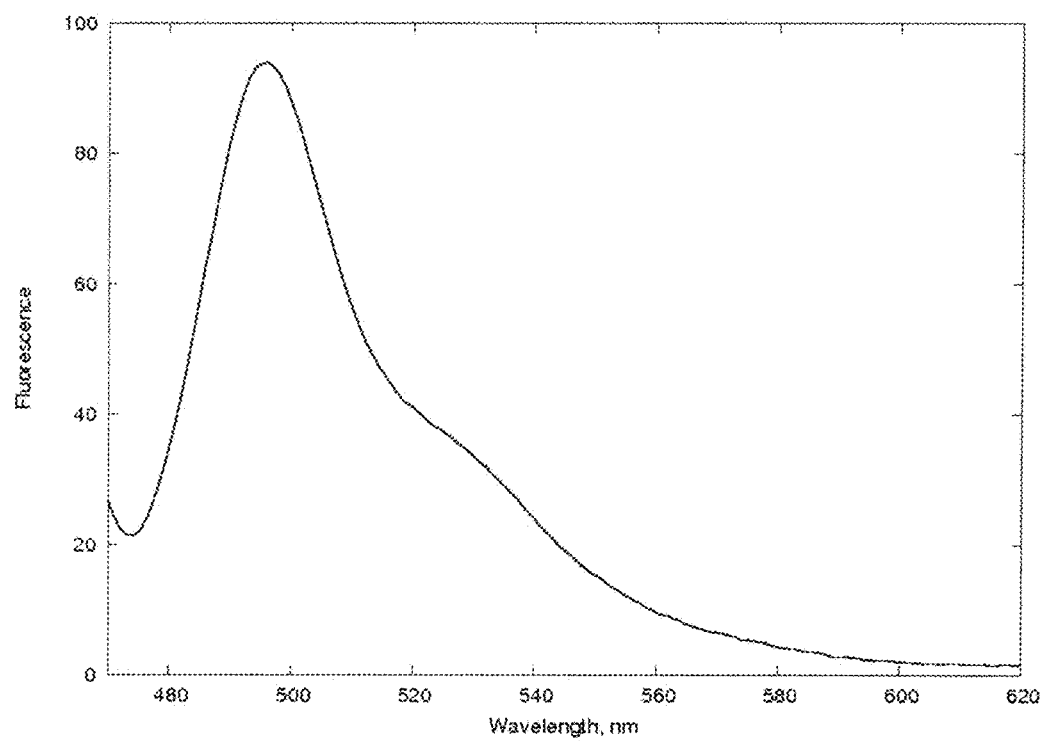
FIG. 4 shows an emission spectrum of a fluorescent protein of SEQ ID NO: 2. Extract from *E. coli* expressing *Rhacostoma* GFP was diluted in 10 mM Tris pH 8.0 buffer to give an absorbance of 0.05 at 466 nm. A fluorescence emission spectrum was collect using a Gilford Fluoro IV spectrofluorometer. The excitation monochromator was set to 466 nm. Fluorescence was recorded in arbitrary units.

The fluorescent E. coli were harvested by centrifugation and the pellet resuspended in a 10 mM Tris pH 8.0 solution with 0.5 mg/ml lysozyme added. After repeated freeze-thaw cycles, the viscous supernatant was pulled through a series of small gauge needles to shear the DNA. Fluorescence excitation and emission spectra were collected and are shown in FIG. 3 and FIG. 4, respectively.

Purification

Whole *E. coli* cells, transformed with the gene for native *Rhacostoma* GFP, and grown in 500 ml of medium in 2.8 L Fernbach flasks, were collected by centrifugation in a refrigerated (4 C) Sorvall centrifuge at 10,000 rpm in 250 mL bottles. The supernatants were discarded and the cell pellets were removed and suspended in an aqueous solution of 1.6 M ammonium sulfate, buffered with 50 mM Tris-HCl at pH 8.0. This buffer also contained 0.02% sodium azide to kill the cells and 0.1% PMSF to block serine proteases from degrading the GFP.

The cell suspension was diluted in the above buffer to a sufficient extent for the next step, (three-phase partitioning), to be most effective. Each of sixteen 50-mL falcon tubes was filled to the 25 mL mark with this suspension. Then 25 mL of t-butanol was added. Each tube was shaken vigorously, by hand, for 60 seconds and then the samples were centrifuged at room temperature in the same Falcon tubes at 3700 rpm in a table-top swinging bucket centrifuge for 20 min. This step produced three distinct phases: (1) a clear, upper organic layer containing 5 mL of water that came from the aqueous ammonium sulfate solution (~30 mL total volume); (2) a robust semi-solid disk (about 3 mm thick); and (3) a clear, green-fluorescent lower liquid phase (~20 mL). The alcohol layer was aspirated away and the congealed, semi-solid disks were lifted out with a spatula. The lower phase was kept. This completes the first stage of three-phase partitioning (TPP).

Fresh t-butanol (30 mL) was added to the aqueous layer, again with vigorous shaking. Further dehydration of the aqueous layer occurred. After centrifugation, as performed in Stage I, there was again an alcohol layer at the top of the tubes (~33 or 34 mL), a paper thin, intensely green disk below, and an aqueous layer below this (~16 mL), almost devoid of GFP. Both liquid layers were aspirated away leaving the thin green disk adhering to the side wall of each Falcon tube. This completes Stage II of TPP.

Next, using a minimum volume of pH 8-buffered 1.6 M ammonium sulfate stock solution, the green disks were serially transferred into a single Falcon tube. Four to five rounds of washing with tiny volumes of stock solution were performed until the GFP was just barely dissolved. This solution was dispensed into 12 microfuge tubes that were then spun at 16,000 rpm for 10 min. This time, four phases appeared after centrifugation. From top to bottom, the following were observed: (1) a clear organic layer; (2) a thin, non-fluorescent white disk; (3) a brilliantly fluorescent, but clear, aqueous layer; and (4) a small pellet at the bottom of the tube. The fluorescent layer was pipetted out, taking care not to include any of the other three phases of material. This completes Stage III of TPP. An absorption spectrum showed the absorbance at 466 nm divided by the absorbance at 277 nm of about 0.87, with a recovery of 101.8 OD's at 466 nm.

The whole TPP sample was applied to a Phenyl Sepharose FF column (16×70 mm=14 mL) in 1.6 M ammonium sulfate buffered to pH 8.0 with TrisHCl (start buffer). After 225 mL of washing with start buffer (16 bed volumes) the absorbance at 277 nm of the final 15 mL fraction had dropped to 0.076 O.D. Units.

Figure 6:
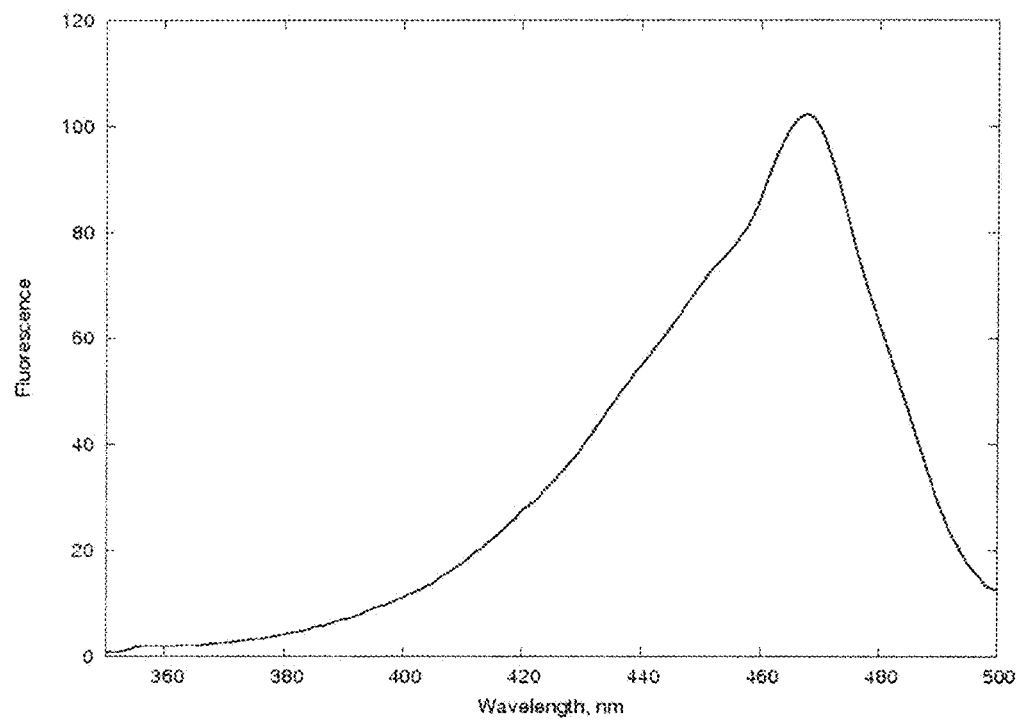
FIG. 6 shows an excitation spectrum of partially purified fluorescent protein from sequence 2. Protein was diluted in 10 mM Tris pH 8.0 buffer to give an absorbance of 0.059 at 466 nm. A fluorescence excitation spectrum was collect using a Gilford Fluoro IV spectrofluorometer. The emission monochromator was set to 505 nm. Fluorescence was recorded in arbitrary units.
Figure 7:
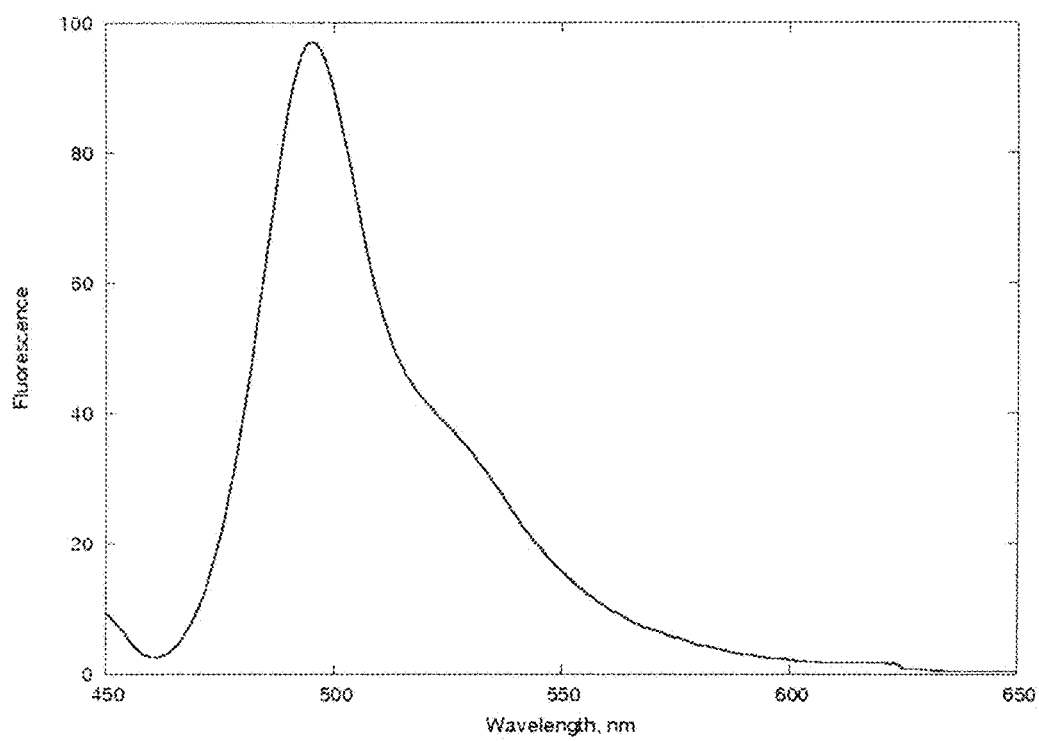
FIG. 7 shows an emission spectrum of partially purified fluorescent protein from SEQ ID NO: 2. Protein was diluted in 10 mM Tris pH 8.0 buffer to give an absorbance of 0.059 at 466 nm. A fluorescence emission spectrum was collect using a Gilford Fluoro IV spectrofluorometer. The excitation monochromator was set to 450 nm. Fluorescence was recorded in arbitrary units.
Figure 8:
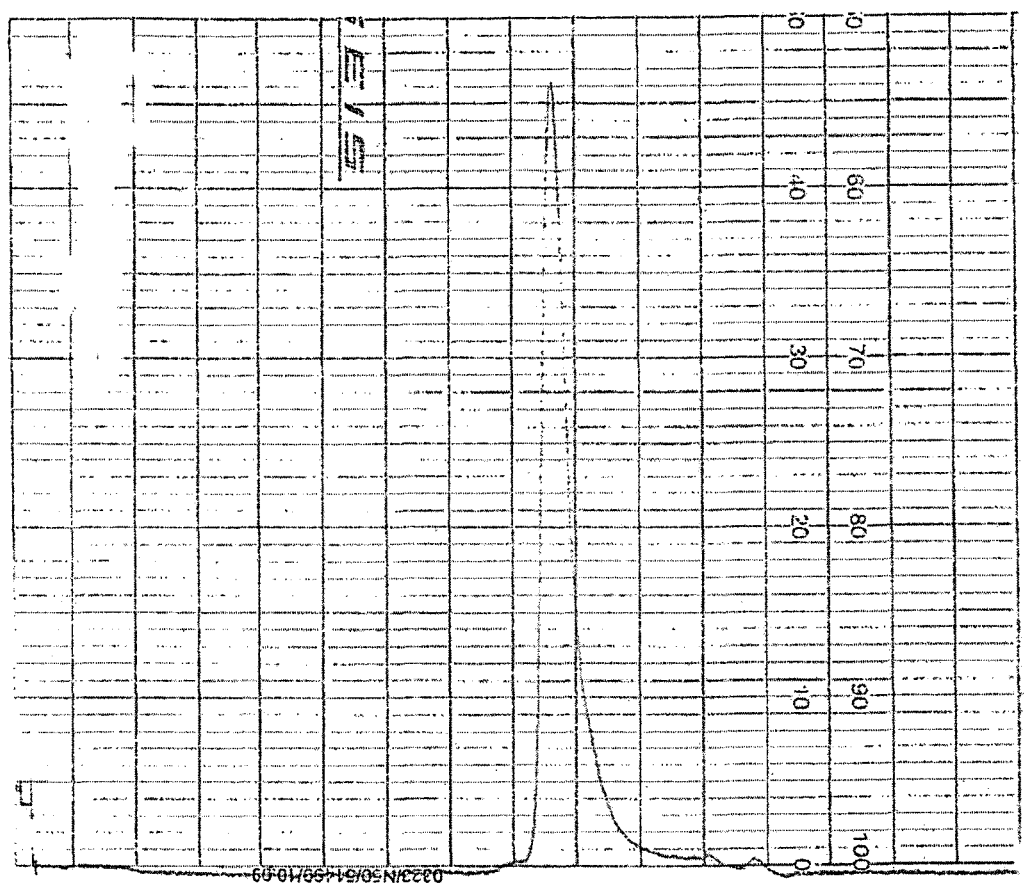
FIG. 8 shows the size exclusion HPLC profile of partially purified fluorescent protein. Full scale is 0.1 AU at 277 nm.

Following this extensive washing step, the ammonium sulfate concentration was dropped to 0.8 M causing the fluorescent protein to elute isocratically. Isocratic elution was continued until the OD 466 dropped to 0.032 (down 100-fold from the peak value of 3.31). After Phenyl Sepharose FF, only the earliest fractions and the terminally pulsed fractions (in dilute Tris buffer) had absorbance ratios significantly below 1.78. Those fractions were excluded from the pool. The absorption spectrum, shown in FIG. 5, has a ratio of absorbance at 466 nm to absorbance at 277 nm of 1.76. A portion was concentrated in a Millipore 10K cutoff spin filter, the fluorescence excitation and emission spectra shown in FIGS. 6 and 7, respectively. A sample of concentrated material was applied to a Phenomenex BioSep SEC-S2000 HPLC column that was run in a buffer of 50 mM sodium phosphate, 100 mM NaCl, 0.02% NaN$_3$ at pH 7.5 (FIG. 8). The column profile shows the majority of the protein in one nearly symmetrical peak. The HPLC profile and the improvement in the A466/A277 ratio indicate a substantial purification of the protein.

The molar extinction coefficient of the fluorescent protein was determined by estimating the chromophore concentration under alkaline conditions. The protein sample was mixed with 1/100 volume of 10 M NaOH and the concentration calculated based on a molar excitation coefficient of 44,100 $M^{-1}$ $cm^{-1}$ at 446 nm for the alkaline-denatured chromophore. (Ward, W. W. 1981. Properties of the coelenterate green fluorescent proteins. In Bioluminescence and Chemiluminescence: Basic Chemistry and Analytical Applications (M. A. DeLuca and W. D. McElroy, eds.) pp. 225-234.)

To generate fluorescent color variants of *Rhacostoma* FP, we used a combination of site-directed and random mutagenesis. Mutation of threonine 203 to tyrosine in wt *Aequorea* GFP contributes, at least in part, to the formation of a yellow fluorescing protein (Tsien R Y. The green fluorescent protein. Annu Rev Biochem. 1998;67:509-44). The *Phialidium* yellow fluorescent protein (Shagin D A, Barsova E V, Yanushevich Y G, Fradkov A F, Lukyanov K A, Labas Y A, Semenova T N, Ugalde J A, Meyers A, Nunez J M, Widder E A, Lukyanov S A, Matz M V. GFP-like proteins as ubiquitous metazoan superfamily: evolution of functional features and structural complexity. Mol Biol Evol. 2004 May; 21(5):841-50. Epub 2004 Feb. 1), one of the closest related to *Rhacostoma*, also has a tyrosine in this position (FIG. 9). We mutated the homologous position in *Rhacostoma* GFP. Mutant V204Y was created by site-directed mutagenesis using a primer overlap extension method (Ho SN, Hunt HD, Horton RM, Pullen JK, Pease L R. Site-directed mutagenesis by overlap extension using the polymerase chain reaction. Gene. 1989 Apr 15;77(1):51-9.). Phusion polymerase (NEB) was used and template DNA was removed by treatment with Dpn I. The resulting mutant was expressed in *E. coli* as described above, but was non-fluorescent or weakly fluorescent. It is likely that additional mutations would be necessary to accommodate the introduction of the tyrosine, so a random mutagenesis approach was employed to identify one or more mutations to restore fluorescence. The non-fluorescent mutant also provided an opportunity to easily select novel fluorescent mutants, as any non-mutated colonies would remain dark when viewed on the surface of a blue-light box. The V204Y mutant was subject to random mutagenesis using the GeneMorph II EZClone Domain Mutagenesis Kit (Agilent Technologies, Inc). The mutated plasmid was transformed into NEB 10 *E. coli* and grown on LB agar plates containing 100 micrograms/ml carbenicillin and 0.1% arabinose. Fluorescent colonies were grown as described above and a portion of the *E. coli* was resuspended in 10 mM Tris buffer pH 8.0. The fluorescence excitation and emission spectra of one such colony is shown in FIG. 11. The excitation peak of the mutant is now in an appropriate region for excitation with the 488 nm line of an argon laser and the emission of the mutated FP was red-shifted by about 8-9 nm. Sequencing revealed the random mutagenesis introduced a methionine to threonine substitution at position 221 (SEQ ID NO: 3 and SEQ ID NO: 4) yielding a double mutant, *Rhacostoma* V204Y M221T. The mutation was red-shifted compared to the wild type, but reduced in intensity or expression by twenty fold or more. Mutation V204Y M221T could serve as a template for subsequent rounds of random or directed mutagenesis.

Results/Description

1. We have identified the nucleic acid sequence and the corresponding amino acid sequence of a novel fluorescent protein similar that that found in *Rhacostoma* atlantica.

2. The novel fluorescent protein was successfully expressed in *E. coli*, demonstrating that the DNA sequence encodes a fluorescent protein. The fluorescence excitation and emission spectra of an *E. coli* extract expressing *Rhacostoma* GFP are shown in FIGS. 3 and 4, respectively.

Figure 5:
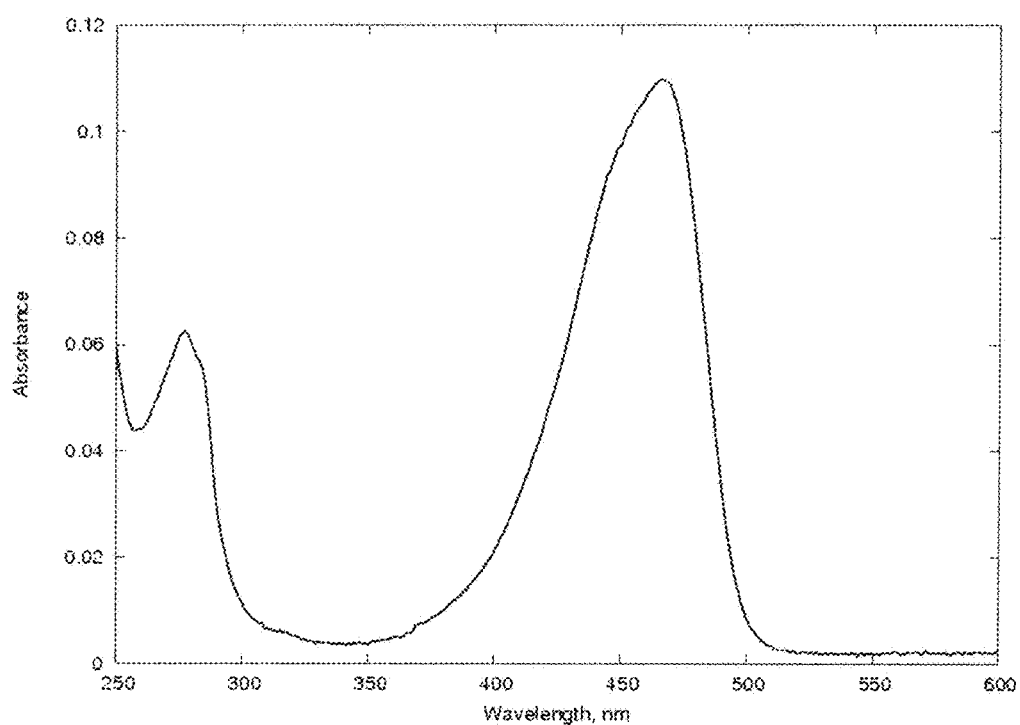
FIG. 5 shows an absorption spectrum of partially purified fluorescent protein from sequence 2. The fluorescent protein was diluted eight-fold into 10 mM Tris pH 8.0 buffer and the absorption spectrum was collected on a Cary 100 spectrophotometer.

3. *Rhacostoma* GFP has an absorption max at about 466 nm (FIG. 5).

4. The excitation spectrum of the wild type *Rhacostoma* GFP is red shifted compared to wild type GFP from *Aequorea victoria*. The extinction coefficient at 466 is 58,000 $M^{-1}$ $cm^{-1}$.

5. FIG. 10 shows the emission spectra of the *Rhacostoma* FP and EGFP excited at the same wavelength and optical density. EGFP is a mutant variant of GFP, having amino acid substitutions F46L and S65T (GFP numbering). (Heim R, Cubitt A B, Tsien R Y. Improved green fluorescence. Nature. 1995 Feb. 23;373(6516):663-4.) The quantum yield of the *Rhacostoma* FP was estimated to be 0.74 by comparison to EGFP at similar optical densities at 450 nm and using a value of 0.6 for the EGFP quantum yield (Clontech).

The emission spectrum of the *Rhacostoma* FP, with a peak in the 495-500 region (FIG. 4, FIG. 7, and FIG. 10), makes this protein a good candidate for FRET assays with fluorescent proteins such as YFP (Tsien R Y. The green fluorescent protein. Annu Rev Biochem. 1998; 67:509-44) and mCitrine (Griesbeck O, Baird G S, Campbell R E, Zacharias D A, Tsien R Y. Reducing the environmental sensitivity of yellow fluorescent protein. Mechanism and applications. J Biol Chem. 2001 Aug 3;276(31):29188-94.). The slightly bluer Cyan Fluorescent proteins (CFPs) can be used as donors for the yellow fluorescent proteins (Day R N, Davidson M W. Fluorescent proteins for FRET microscopy: monitoring protein interactions in living cells. Bioessays. 2012 May; 34(5):341-50.). The CFP, based on *Aequorea* GFP has a tryptophan in the chromophore instead of a tyrosine, and the emission spectra can be very wide, about 60 nm at half height, where the emission spectra of *Rhacostoma* FP is narrow, 33 nm at half height. A narrow emission spectrum could be helpful in FRET assays where emission from the donor chromophore can be problematic. The Teal Fluorescent Protein (TFP) has excitation and emission properties in the same region (Ai H W, Henderson J N, Remington S J, Campbell R E. Directed evolution of a monomeric, bright and photostable version of *Clavularia* cyan fluorescent protein: structural characterization and applications in fluorescence imaging. Biochem J. 2006 Dec 15;400(3):531-40.), but is derived from the *Clavularia* soft coral protein and has only 26% identity with *Rhacostoma* (based on alignment using the ClustalX program and comparing to gi110589865). However, it is interesting to note that the amino acid before tyrosine 69 (*Rhacostoma* numbering) in the chromophore is alanine for both the TFP and the *Rhacostoma* FP, not serine as in GFP (serine 65 in GFP). Thus, the *Rhacostoma* FP provides a new source for development and modification of proteins for use in this color range.

In most of the naturally occurring GFP's, the amino acid found in position 68 of the chromophore possesses an R-group capable of hydrogen bonding to another amino acid. Often that amino acid is a serine. In virtually all cases, a hydrogen bond connects serine 68 to the highly conserved glutamic acid in position 223 (refer to the *Rhacostoma* numbering in FIG. 9). The carboxyl group of glutamic acid 223 projects inward from a beta strand that lies on the perimeter of the beta can. So, in effect, serine (and thus the chromophore) is tethered to the outside rim of the beta can. Unless this beta strand is distorted, the hydrogen bond between serine 68 and glutamic acid 223 regulates the distance between the chromophore imidazolone oxygen and nearby electron withdrawing groups. In the current numbering system, those electron withdrawing groups come from glutamine 95 and arginine 97, both completely conserved in the pile-up diagram of FIG. 9. With a hydrogen bonding serine in position 68, the chromophore is pulled away from glutamine 95 and arginine 97 such that their electrostatic bonds with the chromophore imidazolone is weakened. This allows electrons to flow toward the tyrosine phenolic hydroxyl group, reducing overall electron delocalization and creating a blue spectral shift in excitation and emission. In *Phialidium* GFP (Shagin D A, Barsova E V, Yanushevich Y G Fradkov A F, Lukyanov K A, Labas Y A, Semenova T N, Ugalde J A, Meyers A, Nunez J M, Widder E A, Lukyanov S A, Matz M V. GFP-like proteins as ubiquitous metazoan superfamily: evolution of functional features and structural complexity. Mol Biol Evol. 2004 May; 21(5):841-50. Epub 2004 Feb. 1) and in the *Aequorea* mutant, EGFP, a threonine is substituted for serine in position 68. Now a hydrogen bond is made between the threonine hydroxyl and glutamic acid 223. This substitution provides more "slack" in the hydrogen bond tether, such that the chromophore slips closer to glutamine 95 and arginine 97. A pronounced spectral shift to the red is seen in both cases. (William W. Ward, Biochemical and Physical Properties of Green Fluorescent Protein, in: Green Fluorescent Protein, M. Chalfie and S. Kain, eds. Wiley-Liss 1998, pp. 45-75.)

But in *Rhacostoma* GFP, what is normally a hydrogen bonding amino acid in position 68 is, surprisingly, an alanine. Alanine cannot engage in hydrogen bonding. So, in the same way that tyrosine 68 in *Phialidium* GFP and EGFP permit "slack" in the tether, so does alanine in *Rhacostoma* GFP. So, it appears that the effect of alanine 68 mimics that of threonine 68 in *Phialidium* GFP and EGFP, thus the red shift in all three. Among the 8 GFP's in the FIG. 9 pile-up, there is one other exception—*Obelia* GFP (Aglyamova G V, Hunt M E, Modi C K, Matz M V. Multi-colored homologs of the green fluorescent protein from hydromedusa *Obelia* sp. Photochem Photobiol Sci. 2011 Aug; 10(8)). *Obelia* GFP has a cysteine in this critical position 68. While cysteine is capable of hydrogen bonding, the sulfur atom is larger than a carbon atom. Assuming that the cysteine is hydrogen bonding, the tether may not hold *Obelia* GFP's chromophore close to glutamic acid 223. Thus *Obelia* GFP also displays a red shift.

The new fluorescent proteins developed herein have many uses that include, but are not limited to, the following:

A. As a fluorescent molecular marker. The protein can be expressed in an organism or cell as a fusion protein with a second protein or under direct control of a gene regulator or promoter. The *Rhacostoma* protein is readily expressed in *E. coli* without the need to alter DNA triplet codes for any of the amino acids.

B. In fluorescence resonance energy transfer (FRET) methods. The fluorescent protein can be an energy donor or acceptor. The *Rhacostoma* fluorescent protein is well suited to FRET studies because of its relatively narrow fluorescence emission spectrum (as shown in FIG. 4). A narrow emission spectrum reduces interference with the fluorescence from FRET partners. The narrow fluorescence emission peak in the 495-500 nm region makes the Bii GFP a good candidate for FRET assays with the yellow fluorescent protein.

C. As a reporter molecule attached to a solid support or bead. For example, the protein can be attached to the plate or bead with a peptide linker containing a specific protease cleavage site. Cleavage with the specific protease can result in release of the subject fluorescent protein. The GFPs discussed herein can be used with a GFP-on-a-string protease assay, as discussed in U.S. Pat. No. 7,883,863.

D. Mutagenesis studies. The *Rhacostoma* GFP sequence has been, before the present, an unexplored template for modification. Parameters for exploration include monomer/dimer equilibrium, wavelength of excitation and emission, extinction coefficient, quantum yield, pH sensitivity, rate of maturation, turnover rate, and photostability. The desired property is largely dependent upon the application. For example, a FRET assay may require a blue fluorescence, while in vivo imaging is improved with a far red fluorescence.

Mutation studies have been explored. Some *Rhacostoma* mutations have been designed to generate a monomer protein and a protein with a green, yellow, or red emission. The wild type protein has been characterized with respect to its pH profile, expression level, stability, and monomer/dimer equilibrium. Some mutations have excitation spectra red shifted compared to the wild type protein, potentially overlapping more with the 488 nm argon laser line. Argon lasers are widely used in fluorescence instrumentation such as fluorescence-activated cell sorters. Fluorescent proteins can be useful in cell sorters, either as proteins expressed in the cell, or attached to antibodies or ligands that bind to the outside of the cell. Beads can also be used in cell sorters, using fluorescent proteins to identify the beads.

Additional PCR Details

The Advantage-HF 2 PCR Kit (Clontech Laboratories, Inc.) was used for amplifying DNA from the *Rhacostoma* cDNA library. The thermocycler used was a Minicycler from MJ Research. Unless otherwise stated, the primer concentration was 200 nM. A typical reaction was 94° C. for 90 seconds followed by 26 cycles of 30 seconds at 94° C., 30 seconds at 60° C., and 3 minutes at 72° C.

Primers used for *Rhacostoma* Cloning $1_{st}$ set PCR reactions—*Rhacostoma* library as template

```
>smart_tail1
                                      (SEQ ID NO: 5)
GTGGTATCAACGCAGAGTACTTTTTTTTTTTT >FP202-27 Leptomedusa_primer
                                      (SEQ ID NO: 6)
HGGDRANNTHCCWGTWCCATGGBCWAC
```

Primer FP202-27 was used at 2uM. The reaction was run as above with 26 cycles. The product was then re-amplified for an additional 15 cycles.

$2_{nd}$ set PCR reactions—template was *Rhacostoma* library ligated into pGEM

```
>BGAL primer
                                      (SEQ ID NO: 7)
TGACCATGATTACGCCAAGCTATTTAGGTG >712
                                      (SEQ ID NO: 8)
TGGTAGTGCAGTCATTCCACATCAACG >642
                                      (SEQ ID NO: 9)
CGGCAGTGATGTATTCCACCATCCTC
```

Nested PCR reactions. The first reaction used a primer combination of BGAL/712 followed by BGAL/642 primers. Each was run with 26 cycles.

$3_{rd}$ set PCR—*Rhacostoma* library as template

```
>13
                                      (SEQ ID NO: 10)
CAGCGAGCGATACATCACACACACC

>28
                                      (SEQ ID NO: 11)
CACACACACCAAGAACATTCAAAGTTTCC

>712
                                      (SEQ ID NO: 9)
TGGTAGTGCAGTCATTCCACATCAACG
```

Nested PCR reaction 13/712 followed by 28/712, each at 25 cycles.

$4_{th}$ Set PCR reactions—subclone from pGEM into pBAD

```
>NDE_145
                                      (SEQ ID NO: 12)
CAAACCCATATGAGCACTGGAAAGACTGG

>KPN_145
                                      (SEQ ID NO: 13)
CGGGTACCTTATCCTCCTTTATTATAAGCAGTGTC
```

The reaction was run as above but with 21 cycles.

What is claimed:

1. A fusion protein comprising a fluorescent protein linked to a polypeptide, the fluorescent protein comprising an amino acid sequence with at least 90% sequence identity to the amino acid sequence of SEQ ID NO: 2.

2. The fusion protein of claim 1, wherein the fluorescent protein is a green fluorescent protein (GFP).

3. The fusion protein of claim 1, wherein the fluorescent protein is isolated from an organism of genus *Rhacostoma*.

4. A composition comprising the fusion protein of claim 1.

5. A monomer, dimer or tetramer of the fusion protein of claim 1.

6. The fusion protein of claim 1, wherein the fluorescent protein is encoded by a
    nucleic acid molecule comprising
    a nucleotide sequence that exhibits at least 80% sequence identity to the sequence of nucleotides set forth in SEQ ID NO: 1.

7. The fusion protein of claim 6, wherein the nucleic acid is optimized for expression in human cells, animal cells, bacterial cells, yeast cells, fungal cells, plant cells or insect cells.

8. The fusion protein of claim 6, wherein the nucleic acid is DNA or RNA.

9. A diagnostic composition comprising the fusion protein of claim 1.

10. A method comprising:
    cleaving a fusion protein having a fluorescent protein linked to a polypeptide and having a protease cleavage site, the fluorescent protein including an amino acid sequence with at least 90% sequence identity with the amino acid sequence of SEQ ID NO: 2; and
    expressing the fluorescent protein in a cell.

* * * * *

SEQUENCE LISTING

```
<160> NUMBER OF SEQ ID NOS: 20

<210> SEQ ID NO 1
<211> LENGTH: 717
<212> TYPE: DNA
<213> ORGANISM: Rhacostoma atlantica

<400> SEQUENCE: 1
atgagcactg gaaagactgg taaaatgctc ttccaacaag agattccttt catcgtgtca      60
ttagatggtg aagttgaggg agaaatattt ggtgtcagag gggaaggata tggagatgct     120
```

-continued

| | |
|---|---|
| accattggta agatagacat cacctatcat tgtatcaccg ggaaattgcc agtaccatgg | 180 |
| ccaactattt taacctcact ggcctatgga gtcacatgtt ttgcgaaata tcccgaaaat | 240 |
| gtcaacgatt tctttaaaga ttgtatgcct gaaggctacg tgcaggagag gactatctcg | 300 |
| tttgaaggtg aaggcgtcta taagacacga gcagaagtca cttacgaaag tggaactgtg | 360 |
| tacaacagag tccaattgac tggctctggc ttcaagagaa atgggaacat cctagccaag | 420 |
| aaattggaat tcaatttcaa tccaagttgc agttatgttc ttccagacgc agagaacaat | 480 |
| ggaataaacc ttgtctttaa acaggtgcac aatatcgttg gaggtgattt cattattggc | 540 |
| gagcacgatc agcaaaccag gcccattggc aagggtccgg acgccctccc gcattatcac | 600 |
| catattcagg ttcaaacagt cctctcaaaa gaccctgagg aacccagaga caatatgagg | 660 |
| atggtggaat acatcactgc cgttgactgc gacactgctt ataataaagg aggataa | 717 |

<210> SEQ ID NO 2
<211> LENGTH: 238
<212> TYPE: PRT
<213> ORGANISM: Rhacostoma atlantica

<400> SEQUENCE: 2

```
Met Ser Thr Gly Lys Thr Gly Lys Met Leu Phe Gln Gln Glu Ile Pro
1               5                   10                  15

Phe Ile Val Ser Leu Asp Gly Glu Val Glu Gly Glu Ile Phe Gly Val
                20                  25                  30

Arg Gly Glu Gly Tyr Gly Asp Ala Thr Ile Gly Lys Ile Asp Ile Thr
            35                  40                  45

Tyr His Cys Ile Thr Gly Lys Leu Pro Val Pro Trp Pro Thr Ile Leu
        50                  55                  60

Thr Ser Leu Ala Tyr Gly Val Thr Cys Phe Ala Lys Tyr Pro Glu Asn
65                  70                  75                  80

Val Asn Asp Phe Phe Lys Asp Cys Met Pro Glu Gly Tyr Val Gln Glu
                85                  90                  95

Arg Thr Ile Ser Phe Glu Gly Glu Gly Val Tyr Lys Thr Arg Ala Glu
            100                 105                 110

Val Thr Tyr Glu Ser Gly Thr Val Tyr Asn Arg Val Gln Leu Thr Gly
        115                 120                 125

Ser Gly Phe Lys Arg Asn Gly Asn Ile Leu Ala Lys Lys Leu Glu Phe
    130                 135                 140

Asn Phe Asn Pro Ser Cys Ser Tyr Val Leu Pro Asp Ala Glu Asn Asn
145                 150                 155                 160

Gly Ile Asn Leu Val Phe Lys Gln Val His Asn Ile Val Gly Gly Asp
                165                 170                 175

Phe Ile Ile Gly Glu His Asp Gln Gln Thr Arg Pro Ile Gly Lys Gly
            180                 185                 190

Pro Asp Ala Leu Pro His Tyr His His Ile Gln Val Gln Thr Val Leu
        195                 200                 205

Ser Lys Asp Pro Glu Glu Pro Arg Asp Asn Met Arg Met Val Glu Tyr
    210                 215                 220

Ile Thr Ala Val Asp Cys Asp Thr Ala Tyr Asn Lys Gly Gly
225                 230                 235
```

<210> SEQ ID NO 3
<211> LENGTH: 717
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 3

```
atgagcactg gaaagactgg taaaatgctc ttccaacaag agattccttt catcgtgtca      60
ttagatggtg aagttgaggg agaaatattt ggtgtcagag gggaaggata tggagatgct     120
accattggta agatagacat cacctatcat tgtatcaccg ggaaattgcc agtaccatgg     180
ccaactattt taacctcact ggcctatgga gtcacatgtt ttgcgaaata tcccgaaaat     240
gtcaacgatt tctttaaaga ttgtatgcct gaaggctacg tgcaggagag gactatctcg     300
tttgaaggtg aaggcgtcta taagacacga gcagaagtca cttacgaaag tggaactgtg     360
tacaacagag tccaattgac tggctctggc ttcaagagaa atgggaacat cctagccaag     420
aaattggaat tcaatttcaa tccaagttgc agttatgttc ttccagacgc agagaacaat     480
ggaataaacc ttgtctttaa acaggtgcac aatatcgttg gaggtgattt cattattggc     540
gagcacgatc agcaaaccag gcccattggc aagggtccgg acgccctccc gcattatcac     600
catattcagt atcaaacagt cctctcaaaa gaccctgagg aacccagaga caatatgagg     660
acggtggaat acatcactgc cgttgactgc gacactgctt ataataaagg aggataa        717
```

<210> SEQ ID NO 4
<211> LENGTH: 238
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Met Ser Thr Gly Lys Thr Gly Lys Met Leu Phe Gln Gln Glu Ile Pro
1               5                   10                  15

Phe Ile Val Ser Leu Asp Gly Glu Val Glu Gly Glu Ile Phe Gly Val
                20                  25                  30

Arg Gly Glu Gly Tyr Gly Asp Ala Thr Ile Gly Lys Ile Asp Ile Thr
            35                  40                  45

Tyr His Cys Ile Thr Gly Lys Leu Pro Val Pro Trp Pro Thr Ile Leu
        50                  55                  60

Thr Ser Leu Ala Tyr Gly Val Thr Cys Phe Ala Lys Tyr Pro Glu Asn
65                  70                  75                  80

Val Asn Asp Phe Phe Lys Asp Cys Met Pro Glu Gly Tyr Val Gln Glu
                85                  90                  95

Arg Thr Ile Ser Phe Glu Gly Glu Gly Val Tyr Lys Thr Arg Ala Glu
            100                 105                 110

Val Thr Tyr Glu Ser Gly Thr Val Tyr Asn Arg Val Gln Leu Thr Gly
        115                 120                 125

Ser Gly Phe Lys Arg Asn Gly Asn Ile Leu Ala Lys Lys Leu Glu Phe
    130                 135                 140

Asn Phe Asn Pro Ser Cys Ser Tyr Val Leu Pro Asp Ala Glu Asn Asn
145                 150                 155                 160

Gly Ile Asn Leu Val Phe Lys Gln Val His Asn Ile Val Gly Gly Asp
                165                 170                 175

Phe Ile Ile Gly Glu His Asp Gln Gln Thr Arg Pro Ile Gly Lys Gly
            180                 185                 190

Pro Asp Ala Leu Pro His Tyr His His Ile Gln Tyr Gln Thr Val Leu
        195                 200                 205

```
Ser Lys Asp Pro Glu Glu Pro Arg Asp Asn Met Arg Thr Val Glu Tyr
    210                 215                 220

Ile Thr Ala Val Asp Cys Asp Thr Ala Tyr Asn Lys Gly Gly
225                 230                 235

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtggtatcaa cgcagagtac tttttttttt ttt                              33

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(8)
<223> OTHER INFORMATION: a, c, t, g, unknown or other

<400> SEQUENCE: 6
hggdrannth ccwgtwccat ggbcwac                                     27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgaccatgat tacgccaagc tatttaggtg                                  30

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggtagtgca gtcattccac atcaacg                                     27

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggcagtgat gtattccacc atcctc                                      26

<210> SEQ ID NO 10
<211> LENGTH: 25
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 10
cagcgagcga tacatcacac acacc                                          25

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacacacacc aagaacattc aaagtttcc                                      29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caaacccata tgagcactgg aaagactgg                                      29

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgggtacctt atcctccttt attataagca gtgtc                               35

<210> SEQ ID NO 14
<211> LENGTH: 238
<212> TYPE: PRT
<213> ORGANISM: Aequorea victoria

<400> SEQUENCE: 14

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
            130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
                195                 200                 205

Lys Asp Pro Asn Glu Lys Arg Asp His Met Val Leu Leu Glu Phe Val
            210                 215                 220

Thr Ala Ala Gly Ile Thr His Gly Met Asp Glu Leu Tyr Lys
225                 230                 235

<210> SEQ ID NO 15
<211> LENGTH: 238
<212> TYPE: PRT
<213> ORGANISM: Aequorea coerulescens

<400> SEQUENCE: 15

Met Ser Lys Gly Ala Glu Leu Phe Thr Gly Val Val Pro Ile Leu Ile
1               5                   10                  15

Glu Leu Asn Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Lys Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
            130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
                195                 200                 205

Lys Asp Pro Asn Glu Lys Arg Asp His Met Ile Tyr Phe Glu Phe Val
            210                 215                 220

Thr Ala Ala Ala Ile Thr His Gly Met Asp Glu Leu Tyr Lys
225                 230                 235

<210> SEQ ID NO 16
<211> LENGTH: 237
<212> TYPE: PRT
```

<213> ORGANISM: Aldersladia magnificus

<400> SEQUENCE: 16

Met Ser Lys Gly Ala Glu Leu Phe Thr Gly Ile Val Pro Ile Leu Ile
1               5                   10                  15

Glu Leu Asn Gly Asp Val His Gly His Lys Phe Ser Val Lys Gly Glu
            20                  25                  30

Gly Glu Gly Asp Ala Thr Tyr Gly Lys Leu Glu Ile Lys Phe Val Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ala Arg Tyr Pro Glu His Met Lys Met
65                  70                  75                  80

His Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Ala Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Ser
    130                 135                 140

Tyr Asn Ser His Asn Val Tyr Val Met Ala Asp Lys Pro Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Leu Pro Ile Asn His Tyr Leu Ser Thr Gln Thr Ala Ile Thr
        195                 200                 205

Lys Asp Pro Asn Glu Thr Arg Asp His Met Val Phe Leu Glu Phe Phe
    210                 215                 220

Thr Ala Cys Gly Ile Thr His Gly Met Asp Glu Leu Tyr
225                 230                 235

<210> SEQ ID NO 17
<211> LENGTH: 238
<212> TYPE: PRT
<213> ORGANISM: Aequorea macrodactyla

<400> SEQUENCE: 17

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Phe
    50                  55                  60

Ser Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met

```
            115                 120                 125
Asp Phe Lys Glu Asp Gly Asn Ile Leu Gly His Lys Leu Glu Tyr Asn
130                 135                 140

Phe Asn Ser His Asn Val Tyr Ile Met Pro Asp Lys Ala Asn Asn Gly
145                 150                 155                 160

Leu Lys Val Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Ala Ile Ser
        195                 200                 205

Lys Asp Arg Asn Glu Thr Arg Asp His Met Val Phe Leu Glu Phe Phe
210                 215                 220

Ser Ala Cys Gly His Thr His Gly Met Asp Glu Leu Tyr Lys
225                 230                 235
```

<210> SEQ ID NO 18
<211> LENGTH: 234
<212> TYPE: PRT
<213> ORGANISM: Obelia sp.

<400> SEQUENCE: 18

```
Met Ser Ser Ala Gly Ala Leu Leu Phe Thr Asn Lys Ile Pro Tyr Val
1               5                   10                  15

Thr Glu Leu Glu Gly Asp Val Asn Gly Met Lys Phe Thr Ile His Gly
            20                  25                  30

Lys Gly Thr Gly Asp Ala Ser Thr Gly His Ile Glu Ala Lys Tyr Val
        35                  40                  45

Cys Thr Ser Gly Glu Ile Pro Val Pro Trp Ala Thr Leu Val Ser Thr
    50                  55                  60

Met Cys Tyr Gly Val Gln Cys Phe Ala Lys Tyr Pro Ser His Ile Lys
65                  70                  75                  80

Asp Phe Tyr Lys Ser Ala Met Pro Glu Gly Tyr Ile Gln Glu Arg Thr
                85                  90                  95

Ile Ser Phe Glu Gly Asp Gly Val Tyr Lys Thr Arg Ala Met Val Thr
            100                 105                 110

Tyr Glu Arg Gly Ser Ile Tyr Asn Arg Val Thr Leu Thr Gly Glu Asn
        115                 120                 125

Phe Lys Lys Asp Gly His Ile Leu Arg Lys Asn Val Ala Phe Gln Cys
130                 135                 140

Leu Pro Ser Ile Leu Tyr Ile Leu Pro Asp Thr Val Asn Asn Gly Ile
145                 150                 155                 160

Arg Val Glu Phe Asn Gln Val Tyr Asp Ile Glu Gly Glu Ile Glu Lys
                165                 170                 175

Leu Val Thr Lys Cys Ser Gln Met Asn Arg Pro Leu Ala Glu Ser Ala
            180                 185                 190

Ala Val His Ile Pro Arg Tyr His His Ile Ser Lys His Thr Lys Leu
        195                 200                 205

Ser Lys Asp Leu Asp Glu Arg Arg Asp His Met Cys Leu Val Glu Val
    210                 215                 220

Val Lys Ala Val Asp Leu Asp Thr Tyr Gln
225                 230
```

<210> SEQ ID NO 19
<211> LENGTH: 235

<212> TYPE: PRT
<213> ORGANISM: Clytia gregaria

<400> SEQUENCE: 19

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
                20                  25                  30

Lys Gly Glu Gly Thr Gly Asp Ala Thr Thr Gly Thr Ile Lys Ala Lys
            35                  40                  45

Tyr Ile Cys Thr Thr Gly Asp Leu Pro Val Pro Trp Ala Thr Ile Leu
        50                  55                  60

Ser Ser Leu Ser Tyr Gly Val Phe Cys Phe Ala Lys Tyr Pro Arg His
65                  70                  75                  80

Ile Ala Asp Phe Phe Lys Ser Thr Gln Pro Gly Tyr Ser Gln Asp
                85                  90                  95

Arg Ile Ile Ser Phe Asp Asn Asp Gly Gln Tyr Asp Val Lys Ala Lys
                100                 105                 110

Val Thr Cys Glu Asn Gly Thr Leu Tyr Asn Arg Val Thr Val Lys Gly
            115                 120                 125

Thr Gly Phe Lys Ser Asn Gly Asn Ile Leu Gly Met Arg Val Leu Tyr
        130                 135                 140

His Ser Pro Pro His Ala Val Tyr Ile Leu Pro Asp Arg Lys Asn Gly
145                 150                 155                 160

Gly Met Lys Ile Glu Tyr Asn Lys Ala Phe Asp Val Met Gly Gly Gly
                165                 170                 175

His Gln Met Ala Arg His Ala Gln Phe Asn Lys Pro Leu Gly Ala Trp
                180                 185                 190

Glu Glu Asp Tyr Pro Leu Tyr His His Leu Thr Val Trp Thr Ser Phe
            195                 200                 205

Gly Lys Asp Pro Asp Asp Glu Thr Asp His Leu Asn Ile Val Glu
        210                 215                 220

Val Ile Lys Ala Val Asp Leu Glu Thr Tyr Arg
225                 230                 235
```

<210> SEQ ID NO 20
<211> LENGTH: 234
<212> TYPE: PRT
<213> ORGANISM: Phialidium sp.

<400> SEQUENCE: 20

```
Met Ser Ser Gly Ala Leu Leu Phe His Gly Lys Ile Pro Tyr Val Val
1               5                   10                  15

Glu Met Glu Gly Asn Val Asp Gly His Thr Phe Ser Ile Arg Gly Lys
                20                  25                  30

Gly Tyr Gly Asp Ala Ser Val Gly Lys Val Asp Ala Gln Phe Ile Cys
            35                  40                  45

Thr Thr Gly Asp Val Pro Val Pro Trp Ser Thr Leu Val Thr Thr Leu
        50                  55                  60

Thr Tyr Gly Ala Gln Cys Phe Ala Lys Tyr Gly Pro Glu Leu Lys Asp
65                  70                  75                  80

Phe Tyr Lys Ser Cys Met Pro Glu Gly Tyr Val Gln Glu Arg Thr Ile
                85                  90                  95

Thr Phe Glu Gly Asp Gly Val Phe Lys Thr Arg Ala Glu Val Thr Phe
                100                 105                 110
```

-continued

| | | | | | | | | | | | | | |
|---|---|---|---|---|---|---|---|---|---|---|---|---|---|
| Glu | Asn | Gly | Ser | Val | Tyr | Asn | Arg | Val | Lys | Leu | Asn | Gly | Gln | Gly | Phe |
| | | 115 | | | | | 120 | | | | | 125 | | | |
| Lys | Lys | Asp | Gly | His | Val | Leu | Gly | Lys | Asn | Leu | Glu | Phe | Asn | Phe | Thr |
| | 130 | | | | | 135 | | | | | 140 | | | | |
| Pro | His | Cys | Leu | Tyr | Ile | Trp | Gly | Asp | Gln | Ala | Asn | His | Gly | Leu | Lys |
| 145 | | | | | 150 | | | | | 155 | | | | | 160 |
| Ser | Ala | Phe | Lys | Ile | Met | His | Glu | Ile | Thr | Gly | Ser | Lys | Glu | Asp | Phe |
| | | | 165 | | | | | 170 | | | | | 175 | | |
| Ile | Val | Ala | Asp | His | Thr | Gln | Met | Asn | Thr | Pro | Ile | Gly | Gly | Gly | Pro |
| | | | 180 | | | | | 185 | | | | | 190 | | |
| Val | His | Val | Pro | Glu | Tyr | His | His | Ile | Thr | Tyr | His | Val | Thr | Leu | Ser |
| | | 195 | | | | | 200 | | | | | 205 | | | |
| Lys | Asp | Val | Thr | Asp | His | Arg | Asp | Asn | Met | Ser | Leu | Val | Glu | Thr | Val |
| | 210 | | | | | 215 | | | | | 220 | | | | |
| Arg | Ala | Val | Asp | Cys | Arg | Lys | Thr | Tyr | Leu | | | | | | |
| 225 | | | | | 230 | | | | | | | | | | |